US009956549B1

(12) United States Patent
Patel et al.

(10) Patent No.: US 9,956,549 B1
(45) Date of Patent: May 1, 2018

(54) STABILIZED AND REACTIVE FLUORINATED PHTHALOCYANINE-FUNCTIONALIZED SOLID-STATE SUPPORT COMPOSITES

(71) Applicant: Seton Hall University, South Orange, NJ (US)

(72) Inventors: Hemantbhai Patel, Piscataway, NJ (US); Sergiu M. Gorun, Montclair, NJ (US)

(73) Assignee: Seton Hall University, South Orange, NJ (US)

( * ) Notice: Subject to any disclaimer, the term of this patent is extended or adjusted under 35 U.S.C. 154(b) by 0 days. days.

(21) Appl. No.: 15/055,052

(22) Filed: Feb. 26, 2016

Related U.S. Application Data

(60) Provisional application No. 62/134,748, filed on Mar. 18, 2015.

(51) Int. Cl.
| | |
|---|---|
| C07F 7/02 | (2006.01) |
| B01J 31/18 | (2006.01) |
| B01J 31/26 | (2006.01) |
| C07C 319/14 | (2006.01) |
| C07F 7/08 | (2006.01) |

(52) U.S. Cl.
CPC ............ B01J 31/183 (2013.01); B01J 31/26 (2013.01); C07C 319/14 (2013.01); C07F 7/0834 (2013.01); B01J 2231/70 (2013.01); B01J 2531/845 (2013.01)

(58) Field of Classification Search
CPC .......... C07F 5/069; C07F 5/003; C07F 5/006; C07F 5/025
See application file for complete search history.

(56) References Cited

U.S. PATENT DOCUMENTS

| | | | |
|---|---|---|---|
| 3,039,855 A * | 6/1962 | Urban | C01B 17/05 423/573.1 |
| 5,585,213 A * | 12/1996 | Tamano | C07D 487/22 313/504 |
| 2009/0130050 A1 | 5/2009 | Kanehira et al. | |
| 2013/0064712 A1 | 3/2013 | Roder et al. | |

FOREIGN PATENT DOCUMENTS

WO    WO 2005033110 A1 *    4/2005   ........... C07D 487/22

OTHER PUBLICATIONS

Bench et al., "Introductions of Bulky Perfluoroalkyl Group at the Periphery of Zinc Perfluorophthalocyanine: Chemical, Structural, Electronic, and Preliminay Photophysical and Biological Effects", Angew. Chem. Int. Ed. 2002, 41, No. 5, pp. 747-750.

(Continued)

Primary Examiner — Rosalynd A Keys
(74) Attorney, Agent, or Firm — Lerner, David, Littenberg, Krumholz & Mentlik, LLP

(57) ABSTRACT

A new class of organic-inorganic hybrid composite materials, composites of a fluoroalkyl fluorophthalocyanine and a solid-state support containing an imidazole group. The new class of composite materials can be used as a heterogeneous catalyst for the heterogeneous oxidation organic molecules in aqueous and some organic solvents systems is claimed.

20 Claims, 4 Drawing Sheets

(56) References Cited

OTHER PUBLICATIONS

Bench et al., "Synthesis and Structure of a Biconcave Cobalt Perfluorophthalocyanine and Its Catalysis of Novel Oxidative Carbon-Phosphorus Bonds Formation by Using Air", Angew. Chem. Int. Ed. 2002, 41 No. 5, pp. 750-754.
DeSisto et al., "Preparation and Characterization of a Selective Nitric Oxide Adsorbent Based on Cobalt(II) Phthalocyanine Tetrasulfonic Acid", Ind. Eng. Chem. Res. 2008, 47, 7857-7861.
Folkesson et al., "X-Ray photoelectron spectra and electrochemical properties of imidazol-linked iron phthalocyanine carbon electrode systems", Journal of Applied Electrochemistry 13 (1983) 355-363.
Owens et al., "Adducts of nitric oxide with cobaltous tetraphenylporphyrin and phthalocyanines: potential nitric oxide sorbents", Inorganica Chimica Acta 277 (1998) 1-7.
Patel, Hemantbhai H., "Fluorinated Metallo Phthalocyanines for Chemical and Biological Catalysis", Aug. 2015.

\* cited by examiner

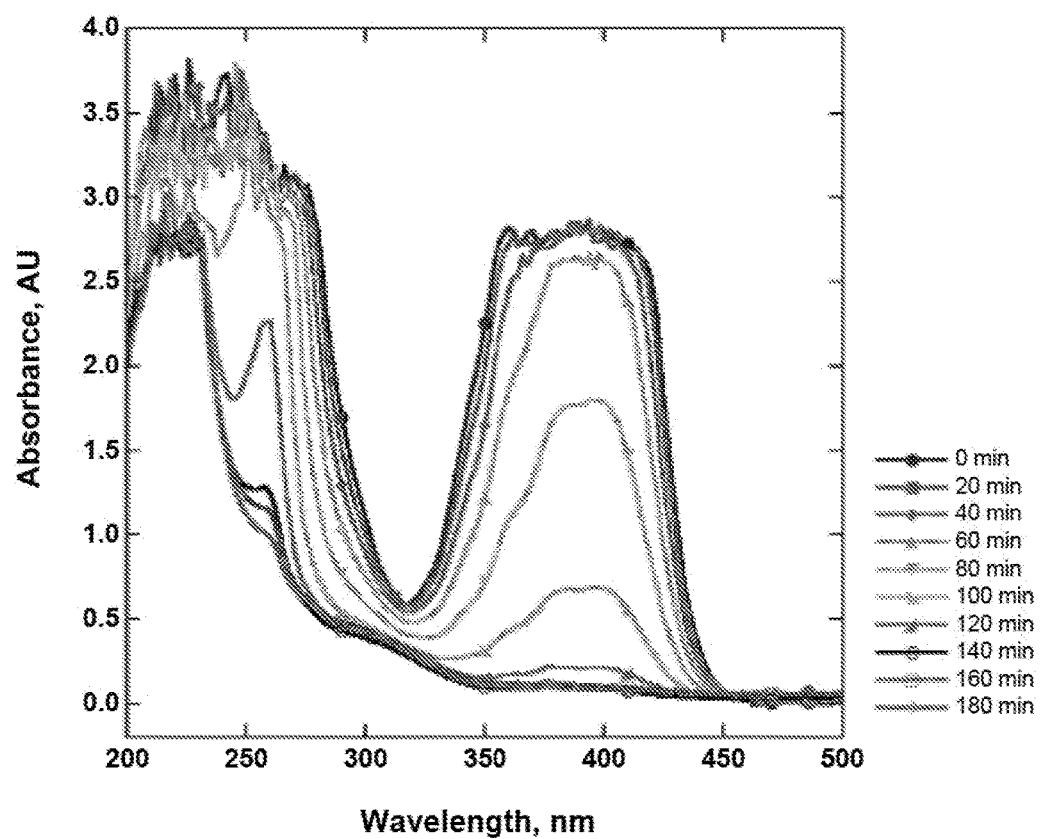
Figure 4. Time dependent UV-Vis Spectrum of AVS.

STABILIZED AND REACTIVE FLUORINATED PHTHALOCYANINE-FUNCTIONALIZED SOLID-STATE SUPPORT COMPOSITES

CROSS-REFERENCE TO RELATED APPLICATIONS

This application claims the benefit of the filing date of U.S. Provisional Patent Application No. 62/134,748 filed Mar. 18, 2015, the disclosure of which is hereby incorporated herein by reference.

BACKGROUND OF THE INVENTION

The synthesis of metal perfluoro alkyl phthalocyanines has been the subject of several disclosures by the inventor S. M. Gorun. Their ability to catalyze oxidations by activating dioxygen chemically in homogeneous solutions, for example for thiols oxidation to disulfide (See US Patent Publication No. 20150315137 to Gorun et al. and incorporated by reference herein) or photochemically in homogeneous solutions or within a polymer matrix have been well documented in the art (See US Patent Publication No. 20150284592 to Gorun et al. and incorporated by reference herein). This ability depends to a large degree on the availability of the metal center for coordination by oxygen and/or reagents, a function that is usually possible due to (i) the kinetic lability of the solvents in which the phthalocyanine is dissolved, and (ii) the absence of a solvent when the phthalocyanines are embedded in a polymer matrix. In other words, in solution the solvents bind weakly or not at all to the metal center. While homogeneous catalysis a valuable process, constructing heterogeneous catalysts that can be easily separated from reactants and products, for example via filtration, or used in solid-gas processes remains a valuable goal for materials science. Heterogenizing a homogeneous catalyst by attaching it to a solid-state support, while desirable does not guarantee retention of reactivity. Phthalocyanine (Pc) materials are conjugated macrocycles known in the art to be chemically or photochemically active. In particular, fluoro alkylated fluoro phthalocyanines are known to exhibit useful aerobic catalytic properties.

With respect to homogeneous vs. heterogeneous catalysis, it is known that unsubstituted phthalocyanines, PcM, where M can be a metal or non-metal, are used as pigments. They exhibit very low solubility in organic solvents. However, as described previously, the introduction of substituents at the periphery of the macrocycle enhances the PcM solubility, bulky substituents being particularly effective due to their ability to prevent intermolecular phthalocyanine π-π aggregation, one of the leading causes of insolubility. Peripheral substituents, however, are required to enhance or reduce the electronic density of the phthalocyanine macrocycles, as required by a particular catalytic process or desired property. While beneficial for homogeneous catalysis, the presence of Pc substituents hinders the use of PcM alone as heterogeneous materials. Depositing phthalocyanines on supports is known in the art, the aim being to prevent their leaching in solution and thus maintaining the heterogeneous nature of a process in which the said phthalocyanine/support participates.

A homogenous catalyst, as stated above, is problematic when it comes to separate it from the useful products into which it is mixed. U.S. Pat. No. 6,511,971 to S. M. Gorun (entitled "Substituted perhalogenated phthalocyanines") and US Patent Publication No. 2015368194 to Gorun et al entitled "System and Method for Fluoralkylated Fluorophthalocyanines with Aggregating Properties and Catalytic Driven Pathway for Oxidizing Thiols," both of which are incorporated by reference herein, describe fluorinated phthalocyanines that are able to bind and activate oxygen in solution. Metal fluorophthalocyanines are capable of forming reactive oxygen species, either via transfer of accumulated photochemical energy to oxygen, or via the transmission electrons provided by other species, for example thiolate anions. The attachment of fluorinated phthalocyanines to a support, for example $SiO_2$ or $TiO_2$, is also known to yield active materials, but they do not function in organic solvents since the phthalocyanines leach out. DeSisto et al, Industrial & Engineering Chemistry Research, 47, 7857 (2008), describe imidazole-functionalized mesoporous silica gel beads that absorb selectively nitric oxide (NO), when a cobalt phthalocyanines substituted with four sulfonic acid interacts with the mesoporous silica. The absorption is essentially irreversible (a single turnover), a process that is inconsistent with a catalytic process that, by definition requires multiple turnovers. Owens et al, Inorganica Chimica Acta, 277, 1 (1998) confirms the instability in non-aqueous solvents of the silica-imidazole phthalocyanine adducts as well as binding of NO. The application envisioned is denitrification.

Folkesson et al, *J. Appl. Electrochem.* 13, 355 (1983) describes electrodes that contain a polymeric phthalocyanine catalyst fixed to an activated carbon carrier by a covalent link of imidazole. The lifetime of the electrode is limited probably due to the splitting of the carbon-imidazole nitrogen bond linking the imidazole to the surface.

The replacement of C—H bonds by C—F bonds, both aromatic and/or aliphatic has resulted in the formation of the phthalocyanine scaffolds of FIG. 1, including the compounds with $R_f = C_3F_7$ (perfluoro isopropyl) and $R_f = R'$, scaffold, as well as $R = H_2N$, scaffold 2. Both scaffolds may accommodate a variety of metal centers, for example, Zn(II), Co(II), Mg(II), Cu(II), Fe(II), Ru(II), Pt(II), Pd(II), Al(III), Ga(III), In(III), V(IV), etc., as the steric ability of the 4 central N to coordinate metal centers is not sterically hindered by the $R_f$, R' ring substituents.

US Patent Publication No. 2013064712 A1 and WO 2011045029 to Roeder et al., describe scaffold 1 complexes that are supported on $SiO_2$, but they remain attached only in the absence of organic solvents. EP19850301973, to Sumitomo teaches the removal of polycyclic aromatic with supported phthalocyanines. The links to the solid-state support are established by covalently bonding the phthalocyanines through any one of various bivalent groups, with a reactive group, such as dihalotriazine, monohalotriazine, trihalopyrimidine, sulfato ethylsulfone, etc.

Considering the above facts, there is a need in the art for catalytic materials that are insoluble in organic solvents and thereby act as heterogeneous oxidation catalysts in such media, with the advantages thereof.

BRIEF SUMMARY OF THE INVENTION

Described herein are stabilized composites of a fluorinated metal phthalocyanine, or mixtures thereof, with a functionalized solid-state support, or mixtures of such supports. The stabilization effect is imparted by a combination of (i) nitrogen bearing functional groups, such as imidazole, covalently linked to an organic or inorganic support, such as a polymer, silica etc., and (ii) fluorinated groups present at the periphery of the phthalocyanine rings, groups that stabilize an anchoring link between the functional group of the support and the metal center of the phthalocyanine via exacerbating the metal Lewis acidity. More particularly, wherein composites exhibit new and unique properties, especially lack of leaching of the phthalocyanine in certain organic solvents, useful in various catalysis applications, such as catalysis based on reactive oxygen species (ROS). The composition synergistically mitigates inhibitory effects of the imidazole-linked support.

The phthalocyanines heavily substituted with hydrophobic groups described herein form stable combinations with a functional support in a way that will prevent the leaching of the phthalocyanine into a solvent in which it would be otherwise soluble and thus act as homogeneous catalysts.

Compositions described herein provide a new class of improved organic-inorganic hybrid composite materials useful as heterogeneous catalysts for generating, depending on the metal center, various reactive oxygen species in aqueous solutions or certain organic solvent and thus performs useful oxidation reactions. The materials are presented schematically in FIG. 2. They can be represented by the general formula FnR'PcML€ Si-Imidazole where n is an integer equal to the sum of all F atoms, whose value is greater than 15 and smaller than 65, R' is a functional group with or without fluorine atoms, or fluorine or fluoroalkyl group, M is a metal center, L stands for an empty metal coordination site or an organic ligand coordinated to M, and Si-Imidazole is the imidazole-functionalized support. The symbol "€" indicates that the left formulation is integrated into the one on the right of the symbol via non-covalent bonding. The organic hybrid composite materials of the subject invention can be a combination of about 0.1 to about 10 weight percent of FnR'PcML with Si-Imidazole, more preferably, 1 weight percent of the fluoroalkyl fluorophthalocyanine of the formulation detailed above, or mixtures thereof, and about 99 weight percent of the solid-state inorganic support.

Additional features and advantages of the present invention are set forth in, or are apparent from the drawings that follow.

BRIEF DESCRIPTION OF THE DRAWINGS

FIG. 4. Time dependent UV-Vis Spectrum of AVS in $D_2O$ in the presence of Si-Imi-$F_{64}$PcZn illuminated with visible light.

Figure 1:
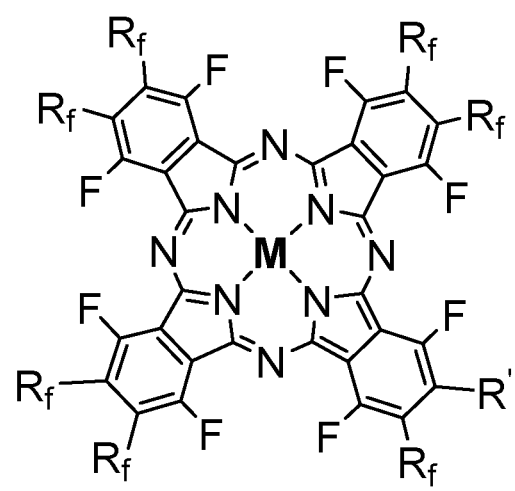
FIG. 1. Representation of fluoroalkyl metal fluorophthalocyanine type materials useful in combination with certain solid-state materials as a component in the present invention.
Figure 2:
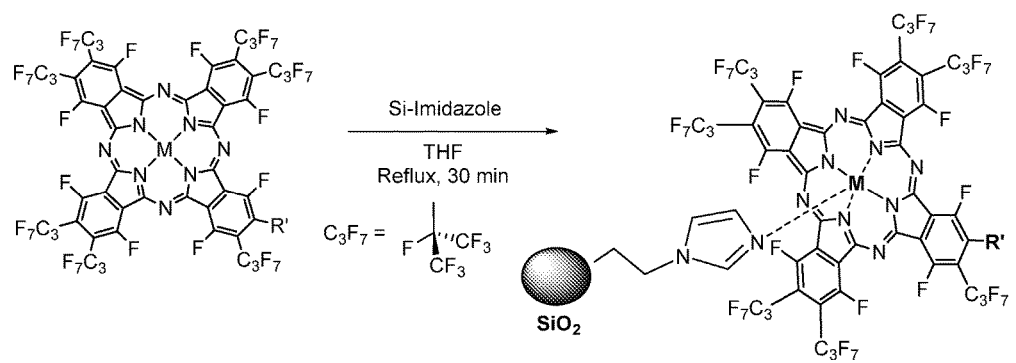
FIG. 2. Schematic representation of hybrid composite material synthesis and structure metal-organic phthalocyanine material—imidazole-$SiO_2$ solid-state support. The dotted line signifies a non-covalent interaction between the metal M and an N atom of the imidazole.

To aid in the understanding of the subject invention, the following examples are provided as illustrative thereof; however, they are merely examples and should not be construed as limitations on the claims.

DETAILED DESCRIPTION

A functionalized fluorine containing phthalocyanine—solid state support composite of the present application can have the formula $(R_f)_{16}$PcM-X. All isomers, e.g., structural isomers, stereoisomers, mirror-image enantiomers, etc. are possible in the above mentioned formula for a functionalized fluorine containing phthalocyanine—solid state support composite of the present application.

In some embodiments, a functionalized fluorine containing phthalocyanine—solid state support composite may be represented by formula (I):

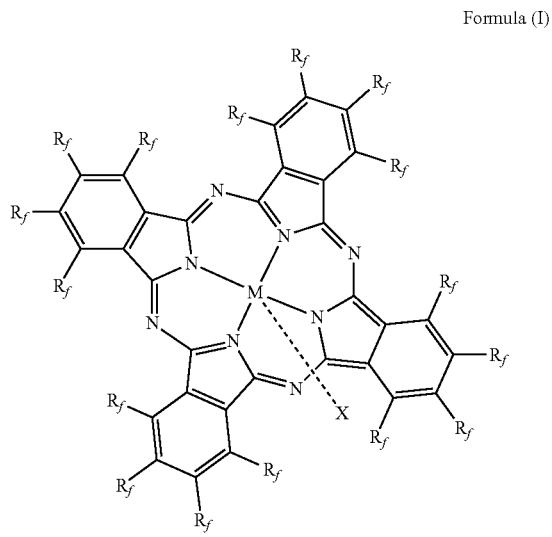

Formula (I)

It should be noted that the formulation $R_f$ is equivalent to the formulation $F_nR'$PcML, but more descriptive. The sum of the F atoms, "n" represents the total numbers of F atoms present in the $R_f$ groups. The "X" ligands is equivalent to the "L" while the definition of the $R_f$ groups, see below, includes that of R.

$R_f$ can be the same or different and can be selected from the group consisting of fluorine (F), a fluorocarbon containing from 1 to 18 carbon atoms, a fluorine containing group, a non-fluorine containing group, and combinations thereof. Exemplary non-fluorine containing groups may include hydrogen, nitro, amino, chloro, sulfonate, thiol, hydroxo, carboxylic, hydrocarbon, or groups that are known in the art to act as aromatic substituents. In one embodiment, a hydrocarbon group can be attached to the aromatic ring of the phthalocyanine, and another non-fluorine containing group can be attached to the hydrocarbon. In some embodiments, at least one $R_f$ contains a fluorine atom. The inclusion of fluorine in at least one $R_f$ can provide higher thermal and chemical stability.

$R_f$ can include fluoroalkyl (e.g., perfluoroalkyl), fluoroalkylcylic, fluoroalkylbicyclic, fluoroaryl, fluoroheteroaryl, fluoroheterocyclic, and fluoroheterobicyclyl. It will be obvious to those skilled in the art that other fluorocarbons having 1 to 18 carbon atoms can be used.

The alkyl group of the fluoroalkyl may be methyl, ethyl, propyl, butyl, cycloalkyl and functionalized alkyl groups. The functionalized alkyl group may be methylamino, dimethylamino, ethylamino, diethylamino, propylamino, butylamino, alkoxy, alkylsulhydryl, haloalkyl and phosphoryl groups. The alkoxy may be methoxy, levulinyl, carboxy, ethoxy, propoxy and functionalized alkoxy groups. The functionalized alkoxy group may be —O($CH_2$)q-R, where q=2-4 and R is —$NH_2$, —$OCH_3$, or —$OCH_2CH_3$. The alkoxyalkyl group may be methoxyethyl, and ethoxyethyl. The haloalkyl group may be —$CF_3$, —$CBr_3$, —$CCl_3$ and —$CI_3$.

The aryl group of the fluoraryl may be phenyl, benzyl, phenol, naphthyl, bi-aryl, trityl, functionalized trityl carbobenzyloxy, functionalized carbobenzyloxy. The functionalized trityl group may be trityl-R, where R is —OC(CH$_3$)$_3$, —OCH$_3$, or —OCH$_2$CH$_3$. The functionalized carboxybenzyloxy group may be selected from the group consisting of CO-aryl-R, where R is a halogen (—Cl, —F, —Br, —I, alkyl or alkoxyalky (—OC(CH$_3$)$_3$, —OCH$_3$, or —OCH$_2$CH$_3$).

The alkylcyclic group of the fluoroalkylcyclic may be cyclopropyl, cyclobutyl, cyclopentyl and cyclohexyl.

The alkylbicyclic group of the fluoroalkylbicyclic may be di-cyclobutyl, di-cyclopentyl and di-cyclohexyl.

The heterocyclic group of the fluoroheterocyclic may be pyrimidinyl, pyrrolo, pyridinyl, oxazolinyl, aza-oxazolinyl, thio-oxazolinyl, thiophenyl, furyl, or imidazolyl.

The heterobicyclic group of the fluoroheterobicyclic may be purinyl, steroyl, indoyl and quinolyl.

M can be a metal or non-metal. The metal is not limited to a diamagnetic metal. Exemplary metals can $Zn^{2+}$, $Mg^{2+}$, low-spin $Fe^{2+}$, $Ru^{2+}$, $Pt^{2+}$, or $Ti^{4+}$. Exemplary non-metals can include $Si^{4+}$.

M can be in complex with, or covalently bound to at least one axial ligand, X, which is the imidazole functionalized support. In some embodiments, M can be in complex with or covalently bound to up to two axial ligands. In one embodiment, X may be represented, in one embodiment, by Formula (II):

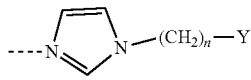

Formula (II)

In Formula II, n can be from one to about 6. In the embodiments described herein n is 3.

Y as represented in Formula (II) can be selected from the group consisting of an oxide, M'$_x$O$_y$, where x and y are small numbers selected such that the overall charge is zero. M' could be, for example, Si, Ti, Zr, for which x=1, y=2; Al for which x=2, y=3 etc. In addition, Y can be a polymer, an inert support (for example charcoal or graphite) etc. In one embodiment Formula II is Si-Imidazole.

Each axial ligand can be any atom or group of atoms, similar or different that can coordinate M. Each axial ligand may be independently selected, and may include H, alkylamino, alkylthio, alkoxy, alkylseleno, alkylsulfonyl, C(S)NHC$_6$H$_{11}$O$_5$, OC(O)CH$_3$, OC(O), CS, CO, CSe, OH, O (oxo) and an alkyl group having from 1 to 12 carbon atoms, or (CH$_2$)$_n$N((CH)$_o$(CH$_3$))$_2$, wherein n is an integer from 1 to 12; and o is an integer from 1 to 11.

In some embodiments, M may be represented by (G)$_a$Y[(OSi(CH$_3$)$_2$(CH$_2$)$_b$N$_c$(R')$_d$(R")$_e$)$_f$X$_g$]$_p$, wherein a is 0 or 1, b is an integer from 2 to 12, c is 0 or 1, d is an integer from 0 to 3, e is an integer from 0 to 2, f is 1 or 2, g is 0 or 1, and p is 1 or 2. Y may be selected from Si, Al, Ga, Ge, or Sn. R' may be selected from H, CH$_3$, C$_2$H$_5$, C$_4$H$_9$, C$_4$H$_8$NH, C$_4$H$_8$N, C$_4$H$_8$NCH$_3$, C$_4$H$_8$S, C$_4$H$_3$O, C$_4$H$_8$Se, OC(O)CH$_3$, OC(O), CS, CO, CSe, OH, C$_4$H$_8$N(CH$_2$)$_3$CH$_3$, (CH$_2$)$_2$N(CH$_3$)$_2$, an alkyl group having from 1 to 12 carbon atoms, and (CH$_2$)$_n$N((CH$_2$)$_o$(CH$_3$))$_2$, wherein n is an integer from 1 to 12; and o is an integer from 1 to 11. R" may be selected from H, SO$_2$CH$_3$, (CH$_2$)$_2$N(CH$_3$)$_2$, (CH$_2$)$_{11}$CH$_3$, C(S)NHC$_6$H$_{11}$O$_5$, an alkyl group having from 1 to 12 carbon atoms, and (CH$_2$)$_n$N((CH$_2$)$_o$(CH$_3$))$_2$, wherein n is an integer from 1 to 12; and o is an integer from 1 to 11. G may be selected from OH and CH$_3$. X may be selected from I, F, Cl, or Br.

M may include at least one metal, at least one non-metal, or a combination of a metal and a non-metal. Exemplary M include AlOSi(CH$_3$)$_2$(CH$_2$)$_3$N(CH$_3$)$_2$, AlOSi(CH$_3$)$_2$(CH$_2$)$_3$N(CH$_3$)$_3$$^+$T$^-$, CH$_3$SiOSi(CH$_3$)$_2$(CH$_2$)$_3$N(CH$_3$)$_2$, HOSiOSi(CH$_3$)$_2$(CH$_2$)$_3$N(CH$_3$)$_2$, HOSiOSi(CH$_3$)$_2$(CH$_2$)$_3$N(CH$_3$)$_3$$^+$T$^-$, Si[OSi(CH$_3$)$_2$(CH$_2$)$_3$N(CH$_3$)$_3$$^+$T$^-$]$_2$, Si[OSi(CH$_3$)$_2$(CH$_2$)$_4$NH$_2$]$_2$, Si[OSi(CH$_3$)$_2$(CH$_2$)$_4$NHSO$_2$CH$_3$]$_2$, HOSiOSi(CH$_3$)$_2$(CH$_2$)$_4$NHSO$_2$CH$_3$, HOSiOSi(CH$_3$)$_2$(CH$_2$)$_3$N(CH$_2$CH$_3$)(CH$_2$)$_2$N(CH$_3$)$_2$, Si[OSi(CH$_3$)$_2$(CH$_2$)$_4$ NHCSNHC$_6$H$_{11}$O$_5$]$_2$, Si[OSi(CH$_3$)$_2$(CH$_2$)$_3$N(CH$_3$)$_2$]$_2$, HOSiOSi(CH$_3$)$_2$(CH$_2$)$_3$OCOCH$_3$, HOSiOSi(CH$_3$)$_2$(CH$_2$)$_3$OH, Si[OSi(CH$_3$)$_2$(CH$_2$)$_3$N(CH$_2$CH$_3$)(CH$_2$)$_2$N(CH$_3$)$_2$]$_2$, HOSiOSi(CH$_3$)$_2$(CH$_2$)$_3$NC$_4$H$_8$O, AlOSi(CH$_3$)$_2$(CH$_2$)$_3$N$^+$(CH$_3$)$_2$(CH$_2$)$_{11}$CH$_3$I$^-$, HOSiOSi(CH$_3$)$_2$(CH$_2$)$_8$N(CH$_3$)$_2$, Si[OSi(CH$_3$)$_2$(CH$_2$)$_3$NC$_4$H$_8$O]$_2$, HOSiOSi(CH$_3$)$_2$(CH$_2$)$_3$NC$_4$H$_8$S, HOSiOSi(CH$_3$)$_2$(CH$_2$)$_3$N(CH$_2$)$_3$(CH$_3$)$_2$, HOSiOSi(CH$_3$)$_2$(CH$_2$)$_3$NCS, HOSiOSi(CH$_3$)$_2$(CH$_2$)$_3$N[(CH$_2$)$_3$N(CH$_3$)$_2$]$_2$, HOSiOSi(CH$_3$)$_2$(CH$_2$)$_3$NC$_4$H$_8$NCH$_3$, Si[OSi(CH$_3$)$_2$(CH$_2$)$_3$NC$_4$H$_8$NCH$_3$]$_2$, HOSiOSi(CH$_3$)$_2$(CH$_2$)$_3$NC$_4$H$_8$N(CH$_2$)$_3$CH$_3$, Si[OSi(CH$_3$)$_2$(CH$_2$)$_3$NC$_4$H$_8$NH]$_2$, or pharmaceutically acceptable salts thereof.

M can include HOSiOSi(CH$_3$)$_2$(CH$_2$)$_3$N(CH$_3$)$_2$, HOSiOSi(CH$_3$)$_2$(CH$_2$)$_3$N(CH$_2$CH$_3$)(CH$_2$)$_2$N(CH$_3$)$_2$, HOSiOSi(CH$_3$)$_2$(CH$_2$)$_3$NC$_4$H$_8$O, HOSiOSi(CH$_3$)$_2$(CH$_2$)$_8$N(CH$_3$)$_2$, or pharmaceutically acceptable salts thereof. In one embodiment, M is HOSiOSi(CH$_3$)$_2$(CH$_2$)$_3$N(CH$_3$)$_2$ or a pharmaceutically acceptable salt thereof. M can be two protons, e.g. H$^+$.

As stated above, the phthalocyanines could produce reactive oxygen species via electron transfer or via transferring accumulated solar energy into dioxygen. The activated oxygen species can react further with a variety of chemical and biological substrates.

In one embodiment, the functionalized fluorine containing phthalocyanine—solid state support composite is suspended either in water or a suitable solvent therefore to create a slurry. The slurry is then combined with the substrate (e.g. the thiol in the example below) on which the phthalocyanine—solid state support composite is intended to operate. Exemplary substrates are described in U.S. Patent Application Publication Nos. 20150284592 and 20150315137. Such substrates are well known to one skilled in the art and not described in detail herein. Once the desired reaction has occurred, the phthalocyanine—solid state support composite is separated from the substrate using conventional separation techniques such as filtration, centrifugation, etc. Such separation techniques are well known to one skilled in the art and not described in detail herein.

In some embodiments, a method for catalytic oxidation of a material can include mixing a inorganic-organic hybrid composite, such as Si-Imi-F$_{64}$PcZn, and the material in a solvent to form a mixture. The mixture can be catalyzing to form of a reactive intermediate species in the mixture. The material can be oxidized by the reactive intermediate species. In some embodiments, the mixture can be illuminated to form the reactive intermediate species. In some embodiments, the material may be selected from the group consisting of a mercaptan, an amino-substituted phenyl compound, and a substituted anthracene. An exemplary mercaptan may be a thiol. An exemplary amino-substituted phenyl compound may be aniline. An exemplary substituted anthracene may be Anthracene-9, 10-bis(ethanesulphonate), sodium salt, dihydrate (AVS).

Example 1

Preparation of $F_nR'PcM$ complexes, FIG. 1. $F_{64}PcM$ complexes, n=64, $R'=R_f=C_3F_7$, M=Co, Zn to be used in subsequent examples, were produced using published procedures [See Bench. B., et al. "Synthesis and structure of a biconcave cobalt perfluorophthalocyanine and its catalysis of novel oxidative carbon-phosphorus bonds formation by using air," *Angewandte Chemie* (2002) 41, 750; Bench, B., et al., "Introduction of bulky perfluoroalkyl groups at the periphery of zinc perfluorophthalocyanine: chemical, structural, electronic, and preliminary photophysical and biological effects," *Angewandte Chemie* (2002) 41, 747, both of which are incorporated by reference herein. The $NH_2F_{51}PcM$ complexes, n=51, $R'=NH_2$, M=Co, Zn were prepared following a published procedure [See Patel, H. PhD Thesis. Seton Hall University, August 2015 which is incorporated by reference herein].

Heterogeneous $F_nR'PcML$ preparation, n=51, $R'=NH_2$, M=Co. The target, $NH_2F_{51}PcCo∈$ Si-Imidazole was prepared by dissolving 10.0 mg of $NH_2F_{51}PcCo$ in 25 mL tetrahydrofuran (THF) and refluxing the mixture for 30 min. 1.0 g of imidazole functionalized silica (3 mmol of imidazole per gm of silica gel) was added and the reaction mixture was refluxed for another 30 min. The weight ratio phthalocyanine/silica gel was 1%, the molar ratio of imidazole/cobalt was 500:1. The functionalized silica gel turned green in color due to the loading of the catalyst and the solution became colorless. The green silica particles were collected by filtration, washed with THF/ethyl acetate and dried in oven at 150° C. for 24 h before use. Heterogeneous $F_nR'PcML$ preparation, n=64, $R'=R_f$, M=Co. The target, $F_{64}PcCo$ ∈ Si-Imidazole was prepared using the same procedure as that used for $NH_2F_{51}PcCo∈$ Si-Imidazole and maintaining the same, 500:1 molar ratio of imidazole/cobalt.

Example 2

The compositions described herein having $SiO_2$—Imidazole supports for fluorinated phthalocyanines are an improvement over fluorinated phthalocyanines with $SiO_2$ supports. In order to illustrate the differences, phthalocyanine leaching experiments were carried out. Firstly, the $NH_2F_{51}PcCo∈$ $SiO_2$ and $F_{64}PcCo∈$ $SiO_2$ composites were prepared by evaporating a suspension of $SiO_2$ in THF solutions of phthalocyanines and drying the solids in an oven at 150° C. for 24 h.

The $NH_2F_{51}PcCo∈$ $SiO_2$ and $F_{64}PcCo∈$ $SiO_2$ solids prepared as described above were suspended in a series of organic solvents including THF, dichloromethane, ethyl acetate, acetone, ethanol, methanol, etc. After stirring for a few minutes the suspensions were filtered and the liquids examined by UV-Vis spectroscopy. The spectra exhibited the trace known for the phthalocyanines used to prepare the solids. In addition, the solids lost their blue-green color and became white. Taken together, the results indicate that the phthalocyanine $SiO_2$ hybrids are unstable in organic solvents regardless of the presence of the functional $H_2N$ group. In contrast, when the same experiment was run using $NH_2F_{51}PcCo∈$ Si-Imidazole and $F_{64}PcCo∈$ Si-Imidazole no leaching was observed, but only when weakly polar or non-polar solvents were used. Examples of other weakly polar solvents include hydrocarbon solvents, a halogenated hydrocarbon solvents, esters, ethers, amides, ketones, etc. Examples of such solvents include dichloromethane, THF, ethyl acetate and acetone. Leaching was observed in more highly polar solvents such as methanol and ethanol.

Example 3

The catalytic oxidation of thiols (mercaptans) was used to demonstrate the catalytic activity of the present composites. The catalysis is related to the MEROX (MERcaptans OXidations) process, widely utilized in the petroleum industry to convert corrosive and foul smelling thiols into disulfide products. The reaction obeys an overall stoichiometry of 4:1, $RSH/O_2$, according to equation 1.

$$4RSH + O_2 \rightarrow 2RSSR + 2H_2O \quad (1)$$

Mechanistically, equations 2-4 outline the solution oxidations. PcCo stands for a phthalocyanine cobalt catalyst. R is a hydrocarbon.

$$2RSH + 2HO^- \rightarrow 2RS^- + 2H_2O \quad (2)$$

$$2RS^- + 2H_2O + O_2 \xrightarrow{PcCo} RSSR + H_2O_2 + 2HO^- \quad (3)$$

$$H_2O_2 + 2RSH \rightarrow RSSR + 2H_2O \quad (4)$$

The process includes very reactive intermediate species: peroxide, $O_2^{2-}$, $RS^\bullet$ radicals and superoxide, $O_2^{\bullet-}$. These species may attack the catalyst.

Figure 3:
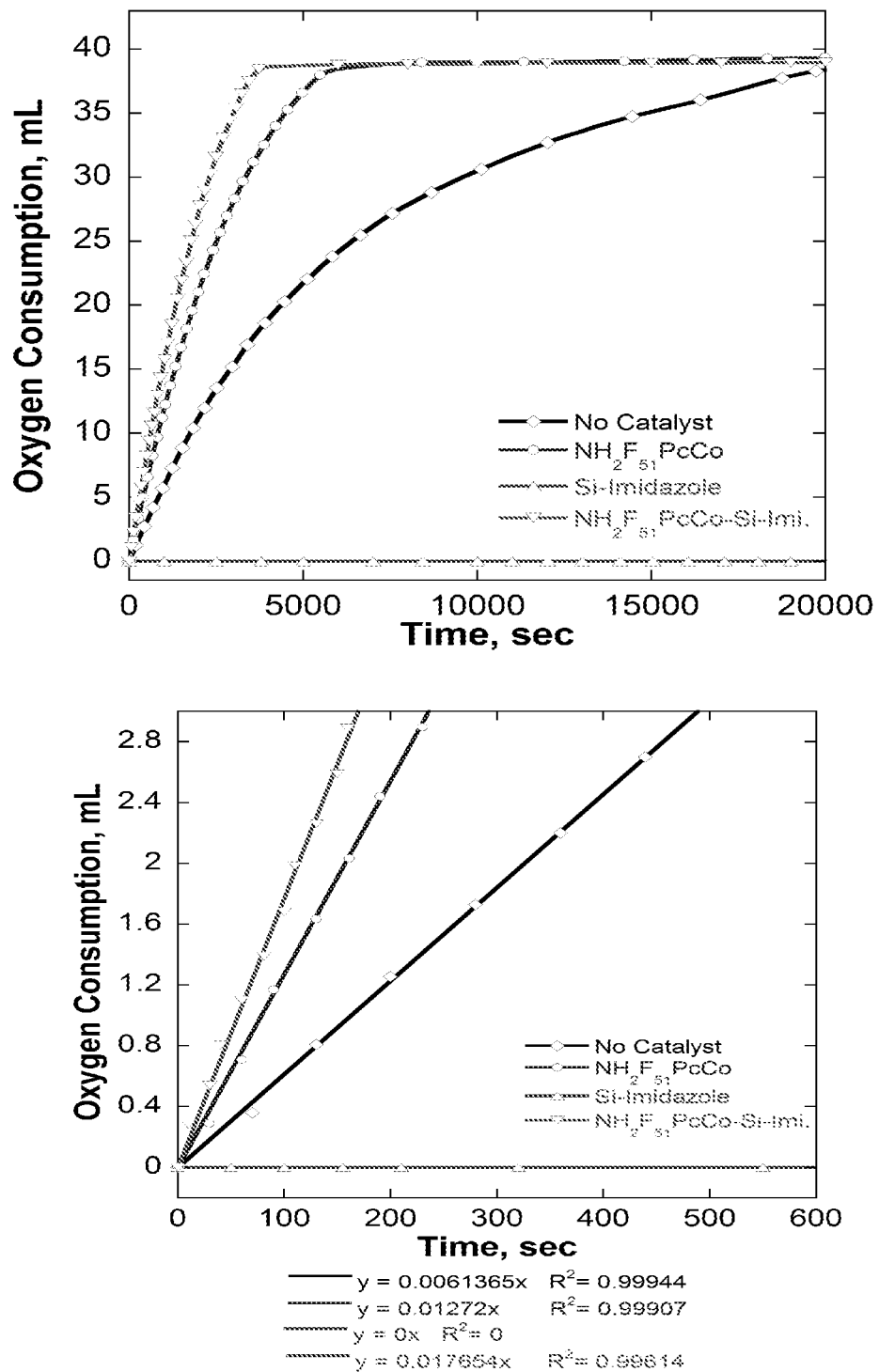
FIG. 3. Graphics of $O_2$ uptake in the aerobic oxidation of 4-fluoro benzene thiol.

Reaction mixtures for thiols oxidations consisted of 50 mL 10±1 μM PcCo in THF and, in case of hybrid catalysts 100.0 mg of $NH_2F_{51}PcCo∈$ Si-Imidazole in 50 mL of THF (1:100 w/w catalyst:silica imidazole ratio), 1 mL NaOH 0.25% (aq) and 7.1 mmol of the thiol of choice, 755 μL 4-fluorobenzene thiol. Volumes under 1 mL were measured with a calibrated micro pipette. The thiol:NaOH:catalyst molar ratio was ~13000:120:1. Oxygen consumption, FIG. 3, was measured with an automatic gas titrator. FIG. 3a shows $O_2$ consumption in the catalyzed auto-oxidation of 4-fluorobenzene thiol in THF. FIG. 3b presents the initial reaction rates, shown as linear fits on the first data points recorded within the first 17 min of each reaction. Table 1 is listing the relevant catalytic parameters.

TABLE 1

Parameters of the catalyzed auto-oxidation of 4-fluorobenzene thiol under $O_2$

| Catalyst | Rate[a] [μmol $O_2$ min$^{-1}$] | TOF[b] [mol RSH s$^{-1}$ mol Pc$^{-1}$] | TON[c] [mol RSH mol Pc$^{-1}$] | TON$_{max}$ [mol RSH mol Pc$^{-1}$] | TON/TON$_{max}$ |
|---|---|---|---|---|---|
| No catalyst | 14.97 | — | 6365* | 7100* | 0.90 |
| $NH_2F_{51}PcCo$ | 31.17 | 4.16 | 12890 | 14200 | 0.91 |
| $NH_2F_{51}PcCo∈Si$-Imidazole | 43.44 | 5.08 | 11225 | 12456 | 0.90 |

[a]Initial reaction rate, μmol $O_2$ min$^{-1}$, calculated from the linear fit portion of the graphs of FIG. 3.
[b]Turnover frequency (TOF), mol substrate s$^{-1}$ mol PC$^{-1}$, calculated under pseudo-first order conditions.
[c]Total oxidation number (TON) after 6 h, calculated stoichiometrically as: (final recorded $O_2$ volume [mL]/molar volume of $O_2$ at 25° C. [24.45 mL mmol$^{-1}$]) × (4000 [μmol substrate mmol $O_2^{-1}$/nPc [μmol Pc]).
*For the non-catalyzed auto-oxidation, turnover number is calculated as: TON = (final recorded $O_2$ volume [mL]/molar volume of $O_2$ at 25° C. [24.45 mL mmol$^{-1}$]) × 4000 [μmol substrate mmol $O_2^{-1}$];
TON$_{max}$ = $n_{RSH}$ = 7100 [μmol substrate].

The data establish that the solid-state hybrid, $NH_2F_{51}PcCo∈$ Si-Imidazole is catalytically active with rate, surprisingly, higher than that of the homogeneous catalyst, $NH_2F_{51}PcCo$. Moreover, as its can be noted from FIG. 3, the support, Si-Imidazole acts actually as an inhibitor, the reaction rate being substantially lower compared with the rate observed in the absence of the support or catalyst. Thus, it is clear that the hybrid, $NH_2F_{51}PcCo$ Є Si-Imidazole exhibits unprecedented synergistic interactions that are beneficial for technological applications. Considering the bonding detailed in Table 1, between the Pc material and the solid-state support, the composite phthalocyanine-solid state support defines a qualitatively new chemical material, i.e. a hybrid that exhibits some properties, including chemical reactive strengths, not found in either of the two components.

Example 4

The production of singlet oxygen was monitored by photolysis of a singlet oxygen trap, Anthracene-9, 10-bis(ethanesulphonate), sodium salt, dehydrate (AVS) to form an endoperoxide product ($AVO_2$) as shown in Scheme 1 below. AVS was selected to detect singlet oxygen production by heterogeneous photo sensitizer $Si-Imi-F_{64}PcZn$. $^1H$ NMR and UV-Vis spectroscopy were used to detect $AVSO_2$.

Scheme 1. Reaction of AVS to form the endoperoxide $AVSO_2$ by trapping singlet oxygen.

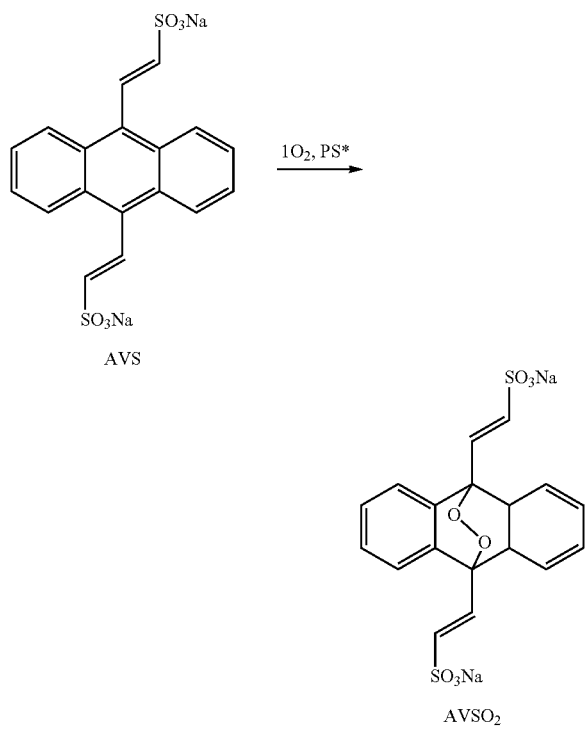

10.85 mg of AVS was dissolved in 25.0 mL of $D_2O$ to form a mixture. 100.0 mg of $Si-Imi-F_{64}PcZn$ was added to the mixture. The mixture was illuminated with a 300 W halogen projector lamp for 3 h under an oxygen balloon at 25° C. The light was filtered with a 0.01M potassium chromate solution to allow only visible light to reach the mixture. The progress of the reaction was monitored by UV-Vis spectroscopy as shown in FIG. 4.

Control experiments that monitored AVS in the absence of $Si-Imi-F_{64}PcZn$ or in the presence of only silica imidazole with $aF_{64}PcZn$ catalyst demonstrated stability in the UV-Vis spectrum and 1HNMR indicated the presence of AVS (not shown). However, Example 4 showed a decrease in the intensity of the 398 nm absorption over a period of 3 hours. This decrease is consistent with the trapping of singlet oxygen by AVS to form $AVSO_2$. Moreover, a preliminary kinetics analysis (not shown) of the reaction reveals $1^{st}$ orders kinetics, which is consistent with the expected changes upon trapping of singlet oxygen. Further catalyst performance was confirmed by $^1H$ NMR (not shown) which was characteristic of the $AVSO_2$, which confirms production of singlet oxygen by $Si-Imi-F_{64}PcZn$.

It will be understood by those skilled in the art that, although the subject invention has been described above in relation to embodiments thereof variations and modifications can be effected in these preferred embodiments without departing from the scope and spirit of the invention.

The invention claimed is:

1. An organic-inorganic hybrid composite including a phthalocyanine moiety coupled to at least one axial ligand, X, wherein the organic-inorganic hybrid composite is represented by Formula I:

Formula (I)

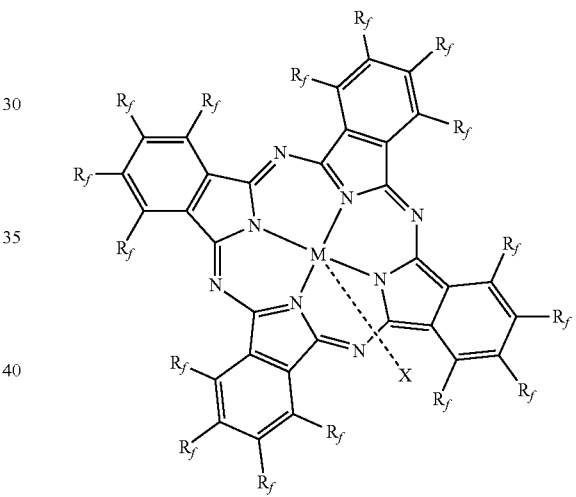

wherein each $R_f$ is independently selected from the group consisting of a fluorine atom, a fluorocarbon group containing from 1 to 18 carbon atoms, a fluorine containing group, a non-fluorine containing group, and combinations thereof, wherein at least one $R_f$ includes a fluorine atom, wherein M is one or more of a metal atom or a non-metal atom, wherein X is represented by Formula II:

(Formula II)

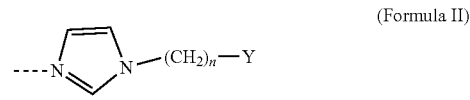

wherein n is from 1 to about 6 wherein Y is selected from the group consisting of an oxide, $M'_xO_y$, a polymer, and an inert material.

2. The organic-inorganic hybrid composite material of claim 1, wherein an amount of X is about 90 to about 99.9 weight percent (wt %), based on the total weight of the organic-inorganic hybrid composite material.

3. The organic-inorganic hybrid composite material of claim 1, wherein the phthalocyanine moiety does not leach in a reaction medium.

4. The organic-inorganic hybrid composite material of claim 3, wherein the reaction medium comprises a solvent.

5. The organic-inorganic hybrid composite material of claim 1, wherein M is a metal in oxidation state of (II), (III), or (IV).

6. The organic-inorganic hybrid composite material of claim 1, wherein $R_f$ is the same or different and is one of perfluoroisopropyl, perfluoropentyl, perfluorohexyl, perfluorooctyl, or isomers thereof or combinations thereof.

7. The organic-inorganic hybrid composite material of claim 1 where n is 3.

8. The organic-inorganic hybrid composite material of claim 1, wherein Y is silicon dioxide ($SiO_2$).

9. The organic-inorganic hybrid composite material of claim 1, wherein Y is an oxide, and the oxide is $M'_xO_y$, wherein x and y are small numbers selected such that the overall charge of $M'_xO_y$ is about zero.

10. The organic-inorganic hybrid composite material of claim 9, wherein M' is selected from the group consisting of silicon (Si), titanium (Ti) and zironcium (Zr) and wherein x=1 and y=2.

11. The organic-inorganic hybrid composite material of claim 9, wherein M' is Al and x=2 and y=3.

12. The organic-inorganic hybrid composite material of claim 1, wherein Y is selected from the group consisting of a polymer and an inert material.

13. A method for catalytic oxidation of a material selected from the group consisting of a mercaptan, an amino-substituted phenyl compound, and a substituted anthracene, comprising:

mixing the composite of claim 1 and the material in a solvent to form a mixture;

catalyzing the formation of a reactive intermediate species in the mixture; and oxidizing the material with the reactive intermediate species.

14. The method of claim 13, wherein the solvent includes water.

15. The method of claim 13, wherein catalyzing the formation of a reactive intermediate species further comprises:

illuminating the mixture to catalyze the formation of the reactive intermediate species.

16. The organic-inorganic hybrid composite material of claim 1, wherein the inert material includes charcoal or graphite.

17. The organic-inorganic hybrid composite material of claim 9, wherein M' is selected from the group consisting of silicon (Si), titanium (Ti), zirconium (Zr) and aluminum (Al).

18. The organic-inorganic hybrid composite material of claim 4, wherein the solvent is selected from the group consisting of dichloromethane, tetrahydrofuran (THF), ethyl acetate and acetone.

19. The organic-inorganic hybrid composite material of claim 4, where the solvent is a non-polar solvent.

20. The organic-inorganic hybrid composite material of claim 1, wherein M includes a metal or non-metal selected from the group consisting of $Zn^{2+}$, $Mg^{2+}$, low-spin $Fe^{2+}$, $Ru^{2+}$, $Pt^{2+}$, $Ti^{4+}$, $Si^{4+}$, $Co^{2+}$, $Sn^{4+}$, $Al^{3+}$, $Ga^{3+}$, $In^{3+}$, and mixtures thereof.

* * * * *